United States Patent [19]
Cunningham

[11] Patent Number: 5,755,810
[45] Date of Patent: May 26, 1998

[54] HIP IMPLANT PROSTHESIS

[76] Inventor: Robert A. Cunningham, 4909 Elm, Bellaire, Tex. 77401

[21] Appl. No.: 748,601

[22] Filed: Nov. 13, 1996

[51] Int. Cl.$^6$ ............................................. A61F 2/32
[52] U.S. Cl. ................................................. 623/23
[58] Field of Search .......................... 623/16, 18, 19, 623/22, 23

[56] References Cited

U.S. PATENT DOCUMENTS

| | | |
|---|---|---|
| Re. 32,471 | 8/1987 | Keller . |
| 3,605,123 | 9/1971 | Hahn . |
| 3,848,272 | 11/1974 | Noiles ................................ 623/23 |
| 3,939,498 | 2/1976 | Lee et al. ........................... 623/23 |
| 4,031,571 | 6/1977 | Heimke et al. . |
| 4,281,420 | 8/1981 | Raab . |
| 4,491,987 | 1/1985 | Park . |
| 4,546,501 | 10/1985 | Gustilo et al. . |
| 4,645,506 | 2/1987 | Link . |
| 4,657,551 | 4/1987 | Ecke . |
| 4,659,067 | 4/1987 | Fournier . |
| 4,714,470 | 12/1987 | Webb, Jr. et al. . |
| 4,718,912 | 1/1988 | Crowninshield . |
| 4,770,660 | 9/1988 | Averill ................................ 623/23 |
| 4,783,192 | 11/1988 | Wroblewski et al. ............. 623/23 |
| 4,813,963 | 3/1989 | Hori et al. . |
| 4,888,023 | 12/1989 | Averill et al. . |
| 4,892,550 | 1/1990 | Huebsch . |
| 4,983,183 | 1/1991 | Horowitz . |
| 4,986,834 | 1/1991 | Smith et al. . |
| 5,004,475 | 4/1991 | Vermeire . |
| 5,013,324 | 5/1991 | Zolman et al. . |
| 5,018,285 | 5/1991 | Zolman et al. . |
| 5,061,287 | 10/1991 | Feiler ................................. 623/23 |
| 5,080,679 | 1/1992 | Pratt et al. . |
| 5,133,772 | 7/1992 | Hack et al. . |
| 5,163,961 | 11/1992 | Harwin .............................. 623/23 |
| 5,171,289 | 12/1992 | Tornier . |
| 5,201,769 | 4/1993 | Schutzer ............................ 623/23 |
| 5,314,492 | 5/1994 | Hamilton et al. ................. 623/23 |
| 5,336,265 | 8/1994 | Serbousek et al. . |
| 5,571,193 | 11/1996 | Kampner ........................... 623/23 |

FOREIGN PATENT DOCUMENTS

| | | | |
|---|---|---|---|
| 2538242 | 6/1984 | France ............................... 623/23 |
| 3833854 | 1/1990 | Germany .......................... 623/23 |

*Primary Examiner*—David Isabella
*Attorney, Agent, or Firm*—James E. Bradley

[57] ABSTRACT

A femoral prosthesis has load shoulders for transferring normal loading to the femur at the proximal end to reduce stress shielding. The femur is resected to provide a flat load shoulder perpendicular to the axis of the femur. The prosthesis has a mating load shoulder in its proximal section which lands on the load shoulders formed in the femur. The prosthesis has a stem that extends downward to a distal end. The intermediate portion of the stem between the distal end and the proximal end is reduced in diameter to add flexibility. The distal end is substantially the diameter of the bone cavity.

13 Claims, 2 Drawing Sheets

HIP IMPLANT PROSTHESIS

TECHNICAL FIELD

This invention relates in general to a bone prosthesis and in particular to a femur prosthesis for a hip implant.

BACKGROUND ART

Hip replacements are very common. In a hip replacement a surgeon will install a prosthesis within the femur. The prosthesis has a stem that inserts into the central cavity of the femur. The stem has a neck that extends obliquely outward. A ball attaches to the neck for location in the acetabulum of the patient. The prosthesis thus replaces the acetabulum joint which deteriorates due to arthritis or other damage.

While hip implants of this nature are successful, often they have to be removed and replaced every few years. One reason is due to stress shielding. Stress shielding occurs as a result of the surface of the stem of the prosthesis being firmly fixed to the inner wall of the femur cavity by gluing, press fitting, bone growth or other means. Under these conditions, when the prosthesis is loaded by the upper body of the user, most of the load is transferred down through the prosthesis to the femur below the prosthesis, and only a small portion is carried through the bone surrounding the prosthesis.

Normally the prosthesis is metal and much more rigid than the bone, as much as 10 to 20 times as stiff. As a result, 80 to 95 percent of the load on the ball is carried by the prosthesis. Only the remaining 5 to 20 percent transfers to the bone surrounding the stem. The portion of the bone that carries only a small portion of the load, which is the portion around the stem in general, partially dissolves over time. This causes a weakened femur and pain to the patient. Remedial work requires additional surgery, expense and inconvenience to the patient.

Various proposals have been made in the past for avoiding stress shielding. These proposals generally involve some means to assure that the bone does not attach to the stem in an intermediate section between distal and proximal ends of the stem. While these work to some extent, improvements are desired.

DISCLOSURE OF THE INVENTION

The prosthesis of this invention has a stem with a proximal section for insertion in the proximal region of the cavity. The proximal region of the cavity is resected so as to provide an upward facing proximal shoulder. The stem has a downward facing shoulder located on its proximal section that mates with the femur shoulder. These shoulders are located generally perpendicular to the axis of the stem, which is substantially congruent with the axis of the femur.

The stem has an intermediate section that extends downward from the proximal section and is sized to provide a significant annular clearance around it within the femur. The lower end or distal section of the stem is sized for a snug fit within the femur cavity. The stem has an obliquely extending neck and a spherical head secured to the upper end of the neck.

In use, a major portion of the load due to the weight of the patient's upper body will pass down from the ball, through the neck and the prosthesis shoulder into the femur shoulder. This transfers a great deal of the load directly to the bone. This transfer, coupled with the lack of any bonding with the bone throughout the length of the intermediate section, avoids stress shielding to a large extent.

The dimensions of the intermediate section are selected so that it will remain approximately congruent with the femur axis even under normal bending. The cross sectional dimension of the intermediate section is made sufficiently small so that the bone and intermediate section will flex approximately equally. The length of the intermediate section must be fairly long to allow flexing to match natural bending of the bone. Preferably this length is approximately two-thirds or more of the total length of the stem from the lower end of the distal section to the shoulder. Because no downward force is transmitted through the intermediate section, the total downward load of the upper body is carried by the bone. In addition, the added flexibility of the bone reduces the lateral force applied by the distal end of the stem to the bone and increases bending stresses to the bone in the area surrounding the stem.

BEST MODE FOR CARRYING OUT THE INVENTION

Figure 1:
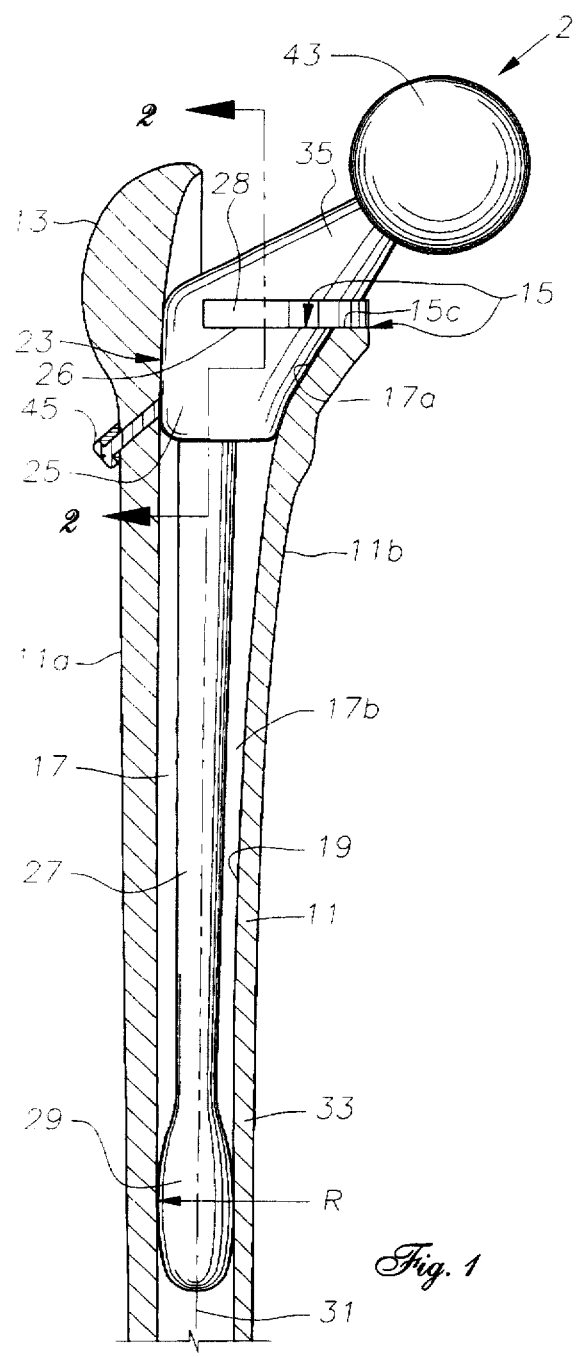
FIG. 1 is a side elevational view of a prosthesis constructed in accordance with this invention installed in a femur.

Referring to FIG. 1, femur 11 has a generally cylindrical exterior which is enlarged on its proximal end 13. For purpose of reference, assuming a patient is facing out of the drawing, femur 11 would be part of the patient's right leg. The exterior of femur can be considered to have a laterally outward facing side 11a, a laterally inward or medial facing side 11b which would face the patient's other femur, a forward or anterior side 11c (FIG. 2) facing out of the drawing, and a rearward or posterior side 11d, shown also in FIG. 2 and facing into the drawing. Proximal end 13 has been resected or cut by bone cutting tools into the configuration shown in FIGS. 1 and 2. The resection results in a femur shoulder 15 that is spaced below the upper end of femur 11. Femur shoulder 15 faces upward and has a forward side portion 15a, a rearward side portion 15b, and an inward side portion 15c. Shoulder 15 has no outward side portion, as the outward portion of proximal end 13 will retain its full length. Shoulder 15 is generally flat and approximately perpendicular to a longitudinal axis of femur 11.

Femur shoulder 15 partially surrounds a proximal region 17a of a cavity. The cavity has an intermediate region 17b which extends downward from proximal region 17a and has generally cylindrical cavity walls 19. Walls 19 are slightly tapered, resulting in a reduction in inner diameter along the length of femur 11.

Figure 3:
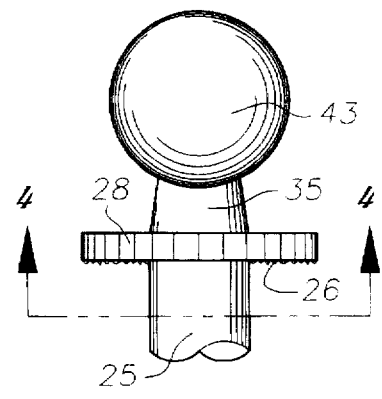
FIG. 3 is a side view of an upper portion of the prosthesis of FIG. 1, shown removed from the femur.
Figure 4:
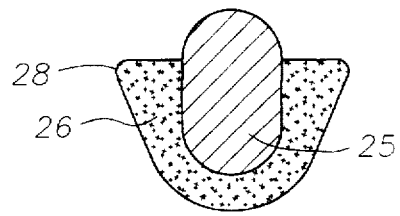
FIG. 4 is a sectional view of the prosthesis of FIG. 1, taken along the line 4—4 of FIG. 3.

A prosthesis 21 is shown installed in femur 11. Prosthesis 21 is a metal member having a stem 23. Stem 23 has a proximal section 25 that locates within cavity proximal region 17a. A downward facing stem shoulder 26 is formed on proximal section 25. As shown also in FIGS. 2 and 3, stem shoulder 26 is the lower surface of a flange 28 that protrudes laterally from proximal section 25. Stem shoulder 26 is flat and oriented for flush engagement with femur shoulder 15. As shown particularly in FIG. 4, stem shoulder 26 is generally formed in a "U" shape, having forward and rearward portions that mate with forward and rearward portions 15a, 15b of the femur shoulder, and an inward side portion that mates with shoulder inward side portion 15c. Also, preferably stem shoulder 26 is roughened to enhance bone growth from femur shoulder 15.

Stem 23 has an intermediate section 27 that extends downward from proximal section 25. Intermediate section 27 has a reduced size diameter substantially smaller than the inner diameter of cavity walls 19. Intermediate section 27 also has a slight generally conical taper so as to substantially match the conical taper of cavity walls 19. This results in an annular clearance between intermediate section 27 and cavity walls 19 that is substantially uniform throughout the length of intermediate section 27.

A distal section 29 is formed on the lower end of intermediate section 27. Distal section 29 has curved generally spherical sidewalls which are formed at a fairly large radius R, as shown in FIG. 1. The radius R is preferably in the range from about six to 10 times the inner diameter of cavity walls 19. The maximum diameter of distal section 29 is substantially the same as the inner diameter of cavity walls 19. The curved exterior sidewalls of distal section 29 engage the generally cylindrical cavity walls 19 in a snug fit. The maximum diameter of distal section 29 is thus substantially larger than the outer diameter of intermediate section 27. A large radius 33 joins intermediate section 27 to distal section 29. Intermediate section 27 and distal section 29 are coaxial along a longitudinal stem axis 31. Shoulder 26 is substantially perpendicular to stem axis 31.

The length and diameter of intermediate section 27 are selected to substantially approximate the flexibility of femur 11. The length of intermediate section 27 is preferably at least two-thirds the length of stem 23 measured along stem axis 31 from the lower end of distal section 29 to shoulder 26. Stem axis 31 is coaxial with the longitudinal axis of femur 11 and remains substantially congruent with the femur axis under bending loads. The annular clearance surrounding intermediate section 27 remains substantially constant under normal bending loads.

Figure 5:
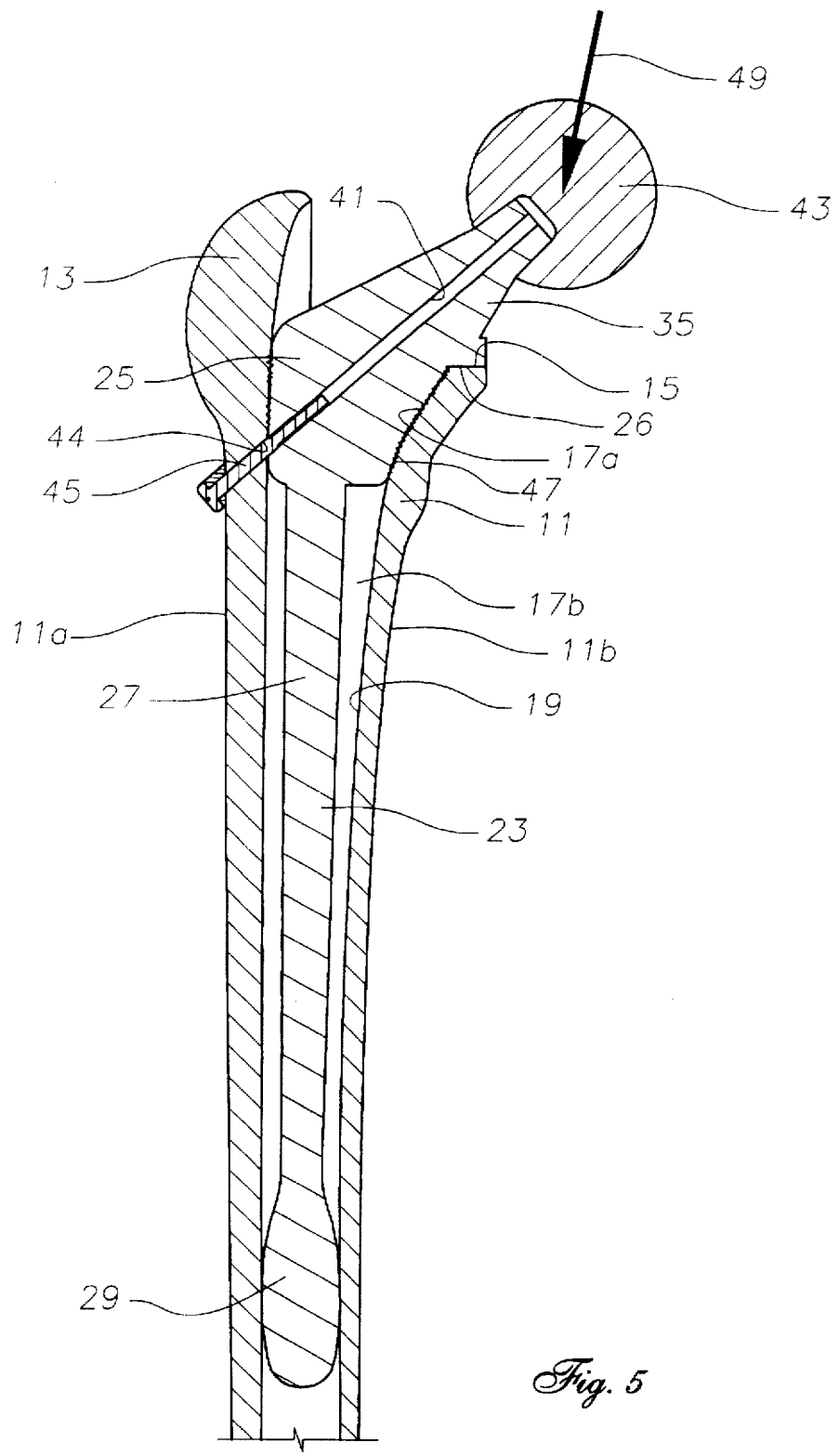
FIG. 5 is a vertical sectional view of the prosthesis of FIG. 1.

Prosthesis 21 has a conventional neck 35 which extends upward and inwardly at an oblique angle relative to stem axis 31. A ball or head 43 secures to the upper end of neck 35 in a locking taper fit in a conventional manner. Referring to FIG. 5, one means for securing prosthesis 21 to femur 11 is shown. This includes an access passage 41 which extends through neck 35, generally parallel with neck 35, and terminates on the outward side of stem proximal section 25. After stem 23 has been inserted into cavity 17, and prior to installing ball 43, the surgeon will insert a long drill through access passage 41 to drill a pilot hole 44 in femur 11. The operator then can insert a fastener 45 through pilot hole 44 and into access passage 41 to secure prosthesis 21 to femur 11. Also, preferably adhesive 47 is employed in cavity proximal region 17a to bond prosthesis proximal section 25 to femur 11. No adhesive should be used at any point below stem proximal section 25, however, as it is important to avoid bonding of intermediate section 27 to femur cavity walls 19.

Figure 2:
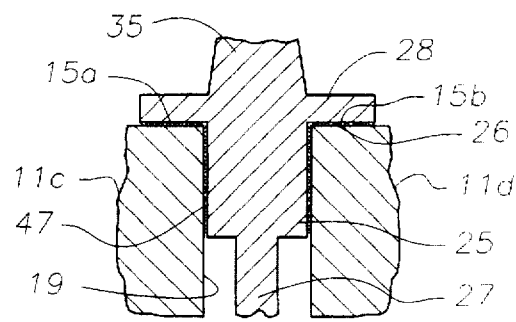
FIG. 2 is a sectional view of the prosthesis and femur of FIG. 1, taken along the line 2—2 of FIG. 1.

To install prosthesis 21, the surgeon will first resect an upper portion of cavity proximal region 17a to the configuration shown in FIGS. 1 and 2. In doing so, he will form a substantially flat, generally U-shaped shoulder 15 with the shoulder being substantially perpendicular to the longitudinal axis of stem 11. The surgeon will clean out cavity 19.

The surgeon then applies adhesive 47 to proximal section 25 and inserts prosthesis 21 to the position shown in FIGS. 1 and 5. Shoulder 26 will land on femur shoulder 15. The surgeon inserts a drill through access passage 41 (FIG. 5), and forms pilot hole 44. The surgeon then mechanically fastens the prosthesis 21 to the bone by inserting a screw or a fastener 45 through pilot hole into threads formed in access passage 41. The surgeon then installs ball 43 and inserts ball 43 into the patient's acetabulum (not shown).

When the person walks, a load will be applied, normally as indicated by the numeral 49 in FIG. 5. Because of the shoulders 15 and 26, most of the load will be transmitted through shoulder 26 and into femur shoulder 15. This load transmits along the length of femur 11. The orientation of shoulders 15, 26, being substantially perpendicular to axis 31, reduces the tendency of slippage between the two shoulders 15, 26. A load in directions other than as indicated by force 49 may occur as a result of climbing, sitting down and other movements. This will result in stresses that will tend to cause shoulders 15, 26 to slip with respect to each other. The firm attachment by fastener 45 and adhesive 47 reduces this possibility.

A lateral reaction force will occur at the contact point between distal section 29 and cavity walls 19. However, as all of the vertical load is transferred through the bone from shoulders 26, 15, rather than through intermediate section 27, the reaction force will be smaller than in the prior art. The flexibility of intermediate section 27 reduces greatly any stress concentration that would otherwise exist at distal section 29. Further, by having a large contact radius R, surface stresses between the prosthesis and bone can be greatly reduced.

The invention has significant advantages. The prosthesis transfers substantially all of the vertical load to the femur in the proximal section. This results in the femur carrying a normal vertical load, not the intermediate section of the stem located between the distal end and proximal section. In addition, bending stresses in the bone are reduced in the same proportion as the vertical load stresses, approximately 80 to 95% throughout the length of the prosthesis stem. The invention provides a maximum reduction of bending stresses on the bone of approximately 50% at the proximal end of intermediate section 27 and gradually restores them to as much as 98% near distal end 29.

By restoring the stresses to the bone as nearly like the original stresses that existed prior to installation of the prosthesis, bone dissolution will be greatly reduced or eliminated altogether. This should allow prosthesis to serve a patient for many years more than the prior art.

I claim:

1. An improved femoral prosthesis for insertion into a femur which has been resected to provide a cavity with a proximal region with an upward facing proximal shoulder at an upper end of the proximal region and a lower region located below the proximal region, the prosthesis comprising:

a stem having a proximal section for insertion in the proximal region of the cavity, the proximal section having an exterior configuration for mating closely with walls of the proximal region of the cavity;

the stem having a flexible section extending downward from the proximal section along a stem axis for insertion in the lower region of cavity, the flexible section having a cross-sectional dimension sized to be surrounded by an annular clearance in the intermediate region of the cavity, the annular clearance extending substantially the entire length of the flexible section;

the stem having a lower end containing a distal section which joins the flexible section and which has a diameter larger than the cross-sectional dimension of the flexible section for lateral stabilizing contact and axial sliding contact with walls of the lower region of the cavity;

a neck extending upwardly and obliquely from the proximal section relative to the stem axis;

a spherical head secured to the neck and adapted for insertion into an acetabulum;

the proximal section having a downward facing substantially flat shoulder extending substantially perpendicular to the stem axis for mating with the proximal shoulder of the femur for transferring to the femur at the proximal shoulder a large portion of downward forces applied to the head; and wherein the stem has a stem length from the downward facing shoulder to a lower end of the distal section, measured along the stem axis, and a flexible section length of the flexible section, the flexible section length being at least two-thirds the stem length, the flexible section length and the cross-sectional dimension of the flexible section being sized throughout the flexible section length to provide flexibility of the flexible section substantially equal to that of the adjacent femur.

2. The prosthesis according to claim 1, wherein:

the proximal section has an anterior side and a posterior side adapted to face in anterior and posterior directions, respectively, relative to the femur; and the shoulder on the proximal section is located on both the anterior and posterior sides of the proximal section.

3. The prosthesis according to claim 1, wherein:

the proximal section has an anterior side, a posterior side, and a medial side adapted to face in anterior, posterior and medial directions respectively, relative to the femur; and the shoulder on the proximal section is located on the anterior, posterior and medial sides of the proximal section.

4. The prosthesis according to claim 9, wherein the stem has a stem length from the lower end of the distal section to the shoulder on the proximal section, measured along the stem axis, and a flexible section length of the flexible section, measured along the stem axis, the flexible section length being at least two-thirds the stem length.

5. The prosthesis according to claim 1, further comprising:

an access hole extending through the proximal section to provide access for drilling a mating pilot hole in the femur, the access hole having a set of threads; and a fastener adapted to extend through the pilot hole formed in the femur into engagement with the threads in the access hole for mechanically securing the proximal section of the stem to the femur.

6. The prosthesis according to claim 5, further comprising:

wherein the neck has a neck axis, and the access hole is coaxial with the neck axis.

7. The prosthesis according to claim 1, wherein the distal section has sidewalls which engage the walls of the cavity and which form a continuous arcuate surface in an axial plane of the stem axis from an upper end of the distal section to the lower end of the distal section.

8. The prosthesis according to claim 7, wherein the sidewalls have a radius of curvature in the axial plane that is within the range of about six to ten times a maximum diameter of the distal section.

9. An improved femoral prosthesis for insertion into a femur which has been resected to provide a cavity which has a proximal region with an upward facing proximal shoulder at an upper end of the proximal region and a lower region located below the proximal region, the prosthesis comprising:

a stem having a proximal section for insertion in the proximal region of the femur, the proximal section having an anterior side and a posterior side which are adapted to contact walls of the proximal region;

the stem having a flexible section extending downward from the proximal section along a stem axis for insertion in the lower region of the femur;

the stem having a lower end containing a distal section which joins the flexible section and which has a diameter larger than a cross-sectional dimension of the flexible section for stabilizing and sliding contact with walls of the lower region of the cavity, the distal section having curved sidewalls which form a continuous arcuate surface in an axial Plane of the stem axis from an upper end of the distal section to a lower end of the distal section;

the cross-sectional dimension of the flexible section being sized to provide an annular clearance between the walls of the cavity and the flexible section so as to provide flexibility of the stem throughout the flexible section substantially equal to that of the adjacent femur;

a neck extending upwardly and obliquely from the proximal section relative to the stem axis;

a spherical head secured to the neck and adapted for insertion into an acetabulum; and a downward facing shoulder protruding in anterior and posterior directions from the anterior and posterior sides, respectively, of the proximal section for mating with the proximal shoulder of the femur for transferring to the femur at the proximal shoulder a large portion of downward forces applied to the head.

10. The prosthesis according to claim 9, wherein the downward facing shoulder is perpendicular to the stem axis.

11. The prosthesis according to claim 9, wherein the neck has a neck axis and wherein the prosthesis further comprises:

a fastener hole extending through the neck and proximal section along the neck axis; and a fastener in the fastener hole for mechanically securing the proximal section of the stem to the femur.

12. The prosthesis according to claim 11, wherein the fastener hole has a threaded section engaged by the fastener.

13. The prosthesis according to claim 9, wherein the sidewalls of the distal section have a radius of curvature in an axial plane of the stem axis that is within the range of about six to ten times a maximum diameter of the distal section.

* * * * *